United States Patent [19]

Cosman

[11] Patent Number: 4,676,255
[45] Date of Patent: Jun. 30, 1987

[54] TELEMETRIC IN-VIVO CALIBRATION METHOD AND APPARATUS USING A NEGATIVE PRESSURE APPLICATOR

[76] Inventor: Eric R. Cosman, 872 Concord Ave., Belmont, Mass. 02178

[21] Appl. No.: 752,315

[22] Filed: Jul. 3, 1985

[51] Int. Cl.[4] ............................................. A61B 5/02
[52] U.S. Cl. .................................................. 128/748
[58] Field of Search ................. 73/701, 715, 717–718, 73/722, 672–675; 128/748

[56] References Cited

U.S. PATENT DOCUMENTS

| | | | |
|---|---|---|---|
| 4,186,751 | 2/1980 | Fleischmann | 128/748 |
| 4,206,761 | 6/1980 | Cosman | 128/748 X |
| 4,393,878 | 7/1983 | Kolin | 128/748 |

*Primary Examiner*—Kyle L. Howell
*Assistant Examiner*—Francis J. Jaworski
*Attorney, Agent, or Firm*—Richard J. Birch

[57] ABSTRACT

A method and apparatus are presented here which extend previous concepts of my patents and papers involving the in-vivo calibration of a telemetric pressure sensor by utilizing variations of positive and negative applied pressures on the skin which overlies the sensor. The sensor has a diaphragm means which, on one side, senses bodily pressure to be measured and, on the other side, senses the pressure under the skin. By pressing or pulling on the skin with positive and negative pressure applied to the outside of the skin, a zero point calibration of the device is achieved, and also a full calibration curve of the device, meaning its diaphragm means movement versus differential pressure across it, can be determined. A design for negative pressure application is also revealed.

9 Claims, 11 Drawing Figures

TELEMETRIC IN-VIVO CALIBRATION METHOD AND APPARATUS USING A NEGATIVE PRESSURE APPLICATOR

BACKGROUND OF THE INVENTION

Described in my U.S. Pat. Nos. 4,206,761, 4,206,762, 4,281,666, 4,281,667, and 4,385,636 was a method of measuring intracranial pressure (ICP) using a known pressure applied to the scalp over the implanted sensor, so as to calibrate the sensor in-vivo, and eliminating the need to know the sensor calibration before implantation. The applied pressure was arbitrary, and no restriction on its value was suggested. In particular, positive or negative applied pressure are equally suitable, as the basic premise of the invention is that the scalp over the sensor transmits pressure faithfully and accurately to the sensor. It was also described in my U.S. Pat. Nos. 4,206,761, 4,206,762, 4,281,666, 4,281,667, and 4,385,636, and in the papers by Zervas, Cosman, and Cosman (1977) and Cosman, et al (1980) that a free-running, continuous readout of the sensor diaphragm displacement, or equivalently some parameter which changes with that displacement, would be a measure of ICP if one calibrated the sensor's response curve by applying the scalp pressure at various values. In the papers above, such continuous graphical recordings were shown for which the pressure axis was calibrated in-vivo in that way.

The need for measuring negative ICP has, in recent years, become more important. This continuation-in-part describes a specific variant of our general method which applies to negative ICP monitoring and for calibration in-vivo of a free-running readout of the sensor diaphragm movement. Thus it is a continuation of previous method and apparatus.

DESCRIPTION OF THE INVENTION

Figure 1:
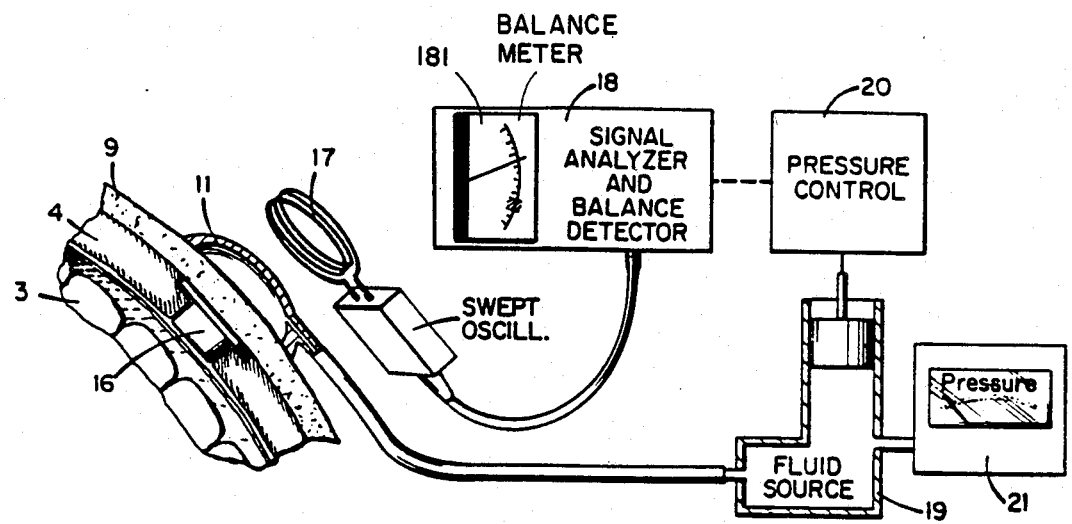
FIG. 1 shows the pressure balancing system as described in U.S. Pat. No. 4,206,761. This is identical to FIG. 3 of that patent, except for the inclusion of a Balance Meter, which is described in the paper by Zervas, et al (1977).
Figure 2:
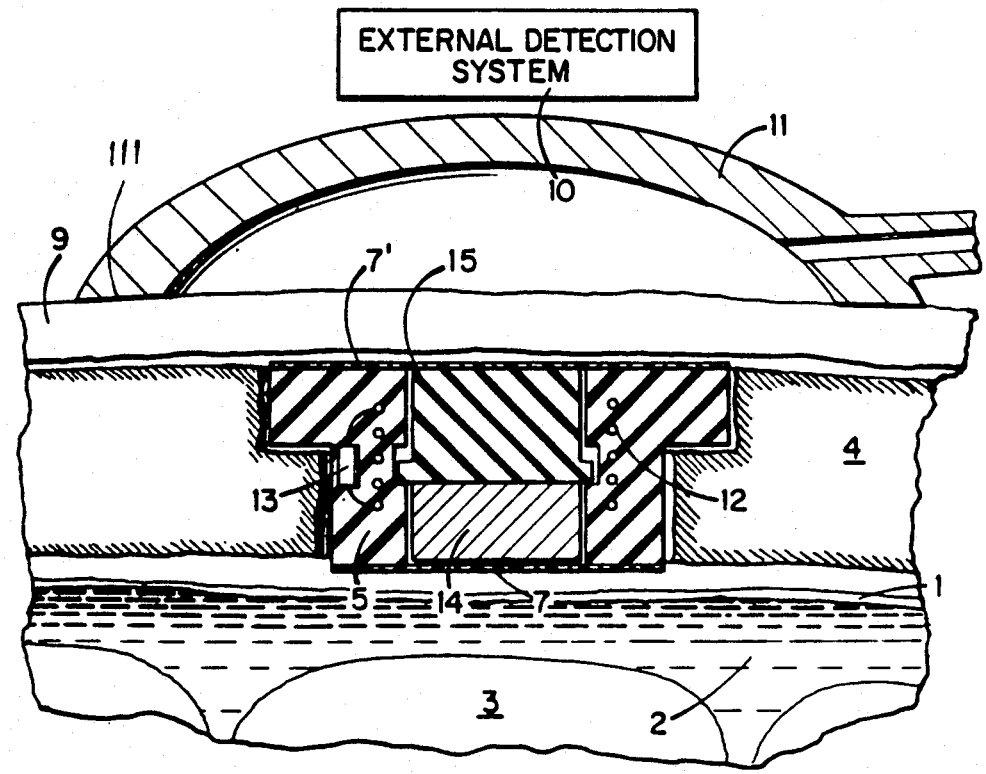
FIG. 2 shows a detailed section view of a double diaphragm type sensor with applied pressure applicator. This is a copy of FIG. 2 of U.S. Pat. No. 4,206,761, the only addition being that of number 111.
Figure 3:
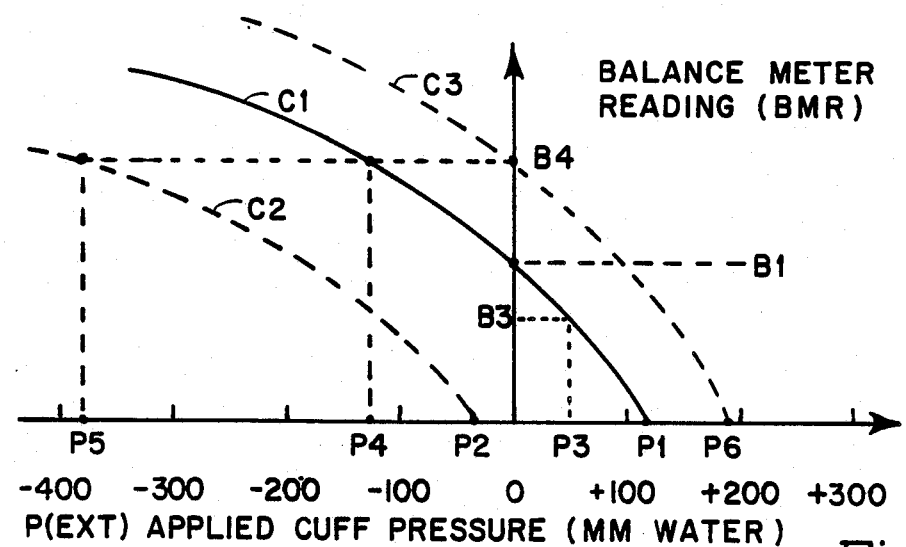
FIG. 3 shows an illustration of "Balance Meter" or diaphragm movement detector signal versus applied pressure over the scalp for three physiologic pressure curves.

FIGS. 1 and 2 are the same as FIGS. 3 and 2, respectively, of U.S. Pat. No. 4,206,761 and illustrate the general method of the invention. An implant 16 is implanted beneath the skin to measure ICP. It has a diaphragm 7' on its top side which communicates with the pressure beneath the scalp 9 which, in turn, equals the pressure P(EXT) which is applied to the outside of the scalp by the applicator 11. 11 is connected to a pressure source 19 which has a readout 21 for measuring the pressure P(EXT) applied to the scalp 9. In addition, the apparati 17 and 18 are means for detecting movement or displacement of diaphragms 7 and 7' or 15 and 14 so that the readout of 18, which is indicated by "Balance Meter" 181 (described in the paper by Zervas et al), gives a measure or signal which changes with displacement or movement of 7' and 15, done by telemetry in which 17 and 18 detect some parameter associated with the movement of 7' or 15 by the associated detection wand 10 or 17. U.S. Pat. Nos. 4,206,761, 4,206,762, 4,281,666, and 4,281,667 describe such means in detail. Also, there may be a stop means of 15 against 5 which stops the movement of 7' or 15 or its cooperatively connected element 14 so that, for a manipulation of the sensor diaphragm 7' and element 15 by pressure P(EXT) applied to the scalp, one can drive element 15 to the stop so that the sensor may be calibrated in-vivo. This could, for instance, be a "zero" calibration where the stop corresponds to a balance of pressures across 7' and 7, i.e. the difference between pressure P(ICP) (the ICP) and the applied pressure P(EXT) on the scalp. It was also taught in the Patents sighted above, and in the paper by Zervas, et al (1977), that a full in-vivo calibration of the sensor 16 plus detector 17 and 18 can be done by varying the applied pressure of P(EXT) and noting the level of the "Balance Meter" reading 181, which is a reading or output of apparatus 18 which indicates movement of diaphragm 7', so that essentially the calibration of that reading versus difference of pressure P=P(ICP)--P(EXT) across diaphragms 7 and 7', which is the ICP relative to atmospheric pressure in the free-running condition when the applied pressure P(EXT) is simply atmospheric, can be determined in-vivo. Note that no restriction was placed on the applied pressures P(EXT) assumed in these papers and patents, and in fact from FIGS. 1 and 2, which are copied from the referenced patents, one sees that the suction on cuff 11 from source 19 would produce a negative pressure P(EXT) on the scalp 9, i.e. a partial vacuum. This would allow negative pressures to be measured by pressure-balancing and a calibration of the sensor's in-vivo response curve, to be determined by observing "Balance Meter" reading versus vacuum pressure read on 21. Indeed, because applicator 11 has no bottom enclosure, i.e. it is not a closed bag, its lower rim 111 (new number) would act as a rough vacuum seal or pressure seal so that the pressure inside 11 is a faithful measure of the applied pressure on 7'. The present continuation-in-part is related to adaptations and methods associated with the use of partial vacuum pressures P(EXT) in the general method above. The present invention has been tested in-vitro for several years and in-vivo in several patients for a comparable period of time.

Figure 4:
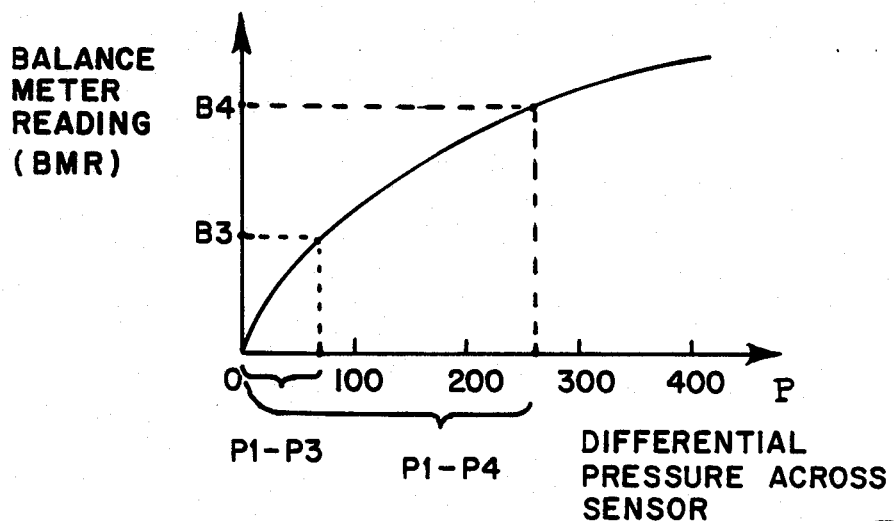
FIG. 4 shows a calibration curve of "Balance Meter" Reading versus differential pressure on the sensor based on the in-vivo calibration as described for FIG. 3.

FIG. 3 illustrates by a graph the in-vivo zero and full curve calibration method described generally in the cited patents and in the paper by Zervas, et al. (1977), but now including the negative pressure domain. Curves C1, C2, C3 are average Balance Meter Readings (BMR), versus applied pressure P(EXT) for three physiologic situations: C2, where the patient has negative ICP (P2); and C1 and C3, where the patient has positive ICP P1 and P6. For C1, when P(EXT)=P(ATM) which is defined as zero, then sensor 16 is said to be "free-running," and B1 represents the BMR at the ICP=P1. This is known for curve C1 because applying P(EXT)=P1 drives the BMR to zero; this is referred to as the "Balance" condition in the sighted references. We also can calibrate the full C1 curve since, by applying pressure P(EXT)=P3, we observe that BMR=B3, and thus we know that differential pressure P=P(ICP)−P(EXT)=P1−P3 corresponds to BMR=B3. In this way, by varying P(EXT), the entire curve C1 can be mapped out or calibrated. Now, by applying a negative P(EXT)=P4 (less than zero), then BMR=B4, and we thus know that P=P1−P4 corresponds to BMR=B4, further extending the calibration range of C1 to higher P. Thus, if ICP rises from P1 to P6=P1−P4 as portrayed by curve C3, then the BMR=B4 for that ICP in free-running state. By this process, one can determine a free-running calibration curve from C1 in-vivo corresponding to a BMR versus ICP. In C2, the patient has negative ICP=P2, known by applying negative pressure until element 15 rises off of its stop position at pressure P2. Again, making P(EXT) more negative will make the BMR rise as it did for C1, and, for instance, at P5 it could assume level B4. If C1 is the same shape curve as C2, then P2−P5 will equal P1−P4. Thus knowing C1 from one calibration procedure as described above, it can provide them a general in-vivo calibration curve as shown in FIG. 4. That curve is the same shape as the curve of FIG. 3, but it is reflected about the ordinate axis. Such a curve could be programmed into apparatus 18 so that a linear display 181 or corresponding chart recording of ICP could be gotten from the BMR readings automatically.

Figure 5:
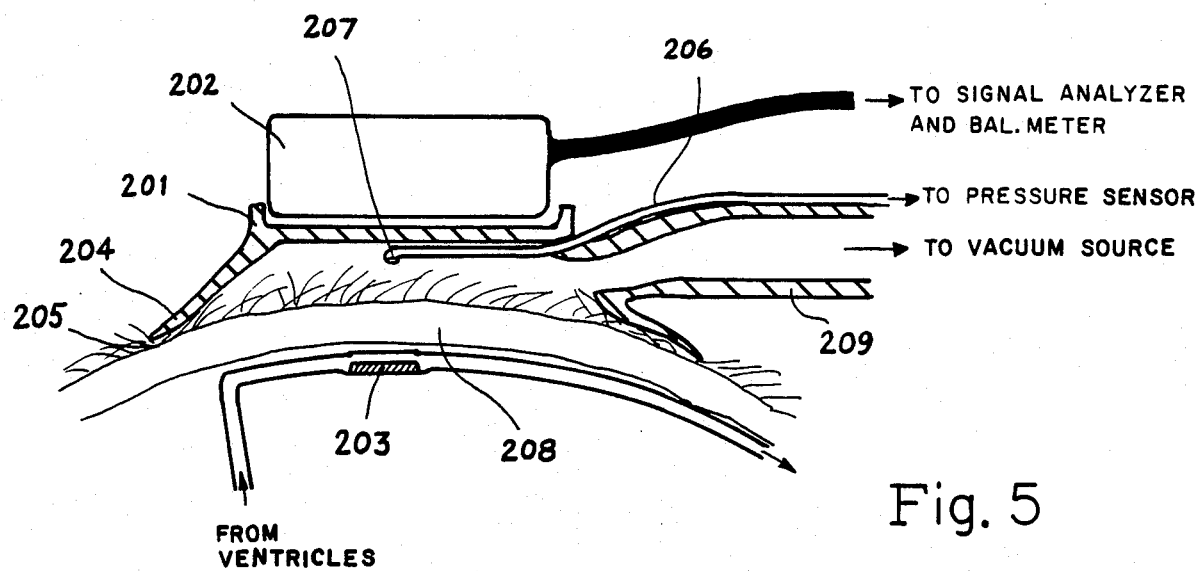
FIG. 5 shows a design in sectional view of a partial vacuum applicator for the skin.

FIG. 5 shows a design for a negative or positive pressure applicator cuff 210 beneath antenna, detector, or "wand" 202 interrogating sensor 203 of ventricular ICP, similar to that in the patents referred to above. 201 has an apron 204 that follows the scalp or hair contour 205 to increase leak resistance between 204 and 205. A detector channel 206 goes to a pressure sensor in apparati 19, 20, and 21 of FIG. 1, and it has an opening 207 to detect pressure just above the scalp 208 for best accuracy. The entrance line 209 goes to a continuous flow pressure source, either positive pump or negative vacuum pump (such as in a vacuum cleaner) analogous to 19 and 20 in FIG. 1. Either pump may have variable power control or automatic cycling program for manual or automatic pressure ICP measurement or calibration cycle as discussed above. The automatic process could be controlled by computer or analogous means.

Figure 6A:
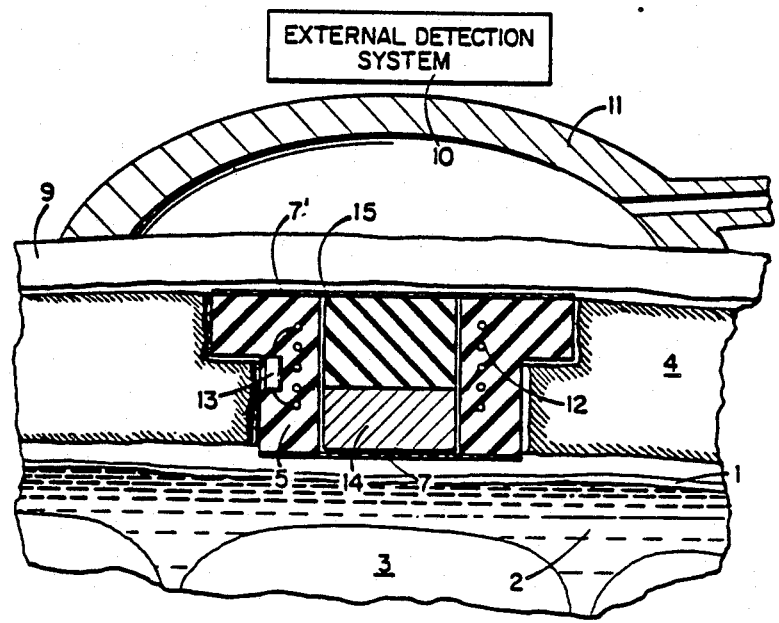
FIGS. 6(a) and 6(b) show schematic diagrams of two and one diaphragm pressure sensors which do not have built-in stop means within them at zero pressure. These are identical to FIG. 2 of U.S. Pat. No. 4,206,761 and FIG. 7 of U.S. Pat. No. 4,385,636, except that the stop position is removed for the planar or zero position of the diaphragm(s).
Figure 6B:
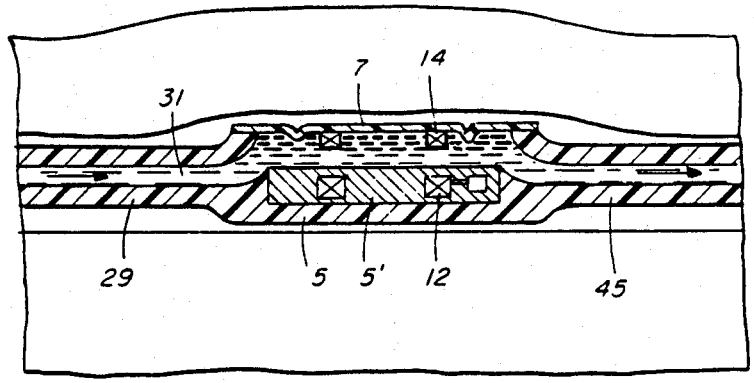
Figure 7:
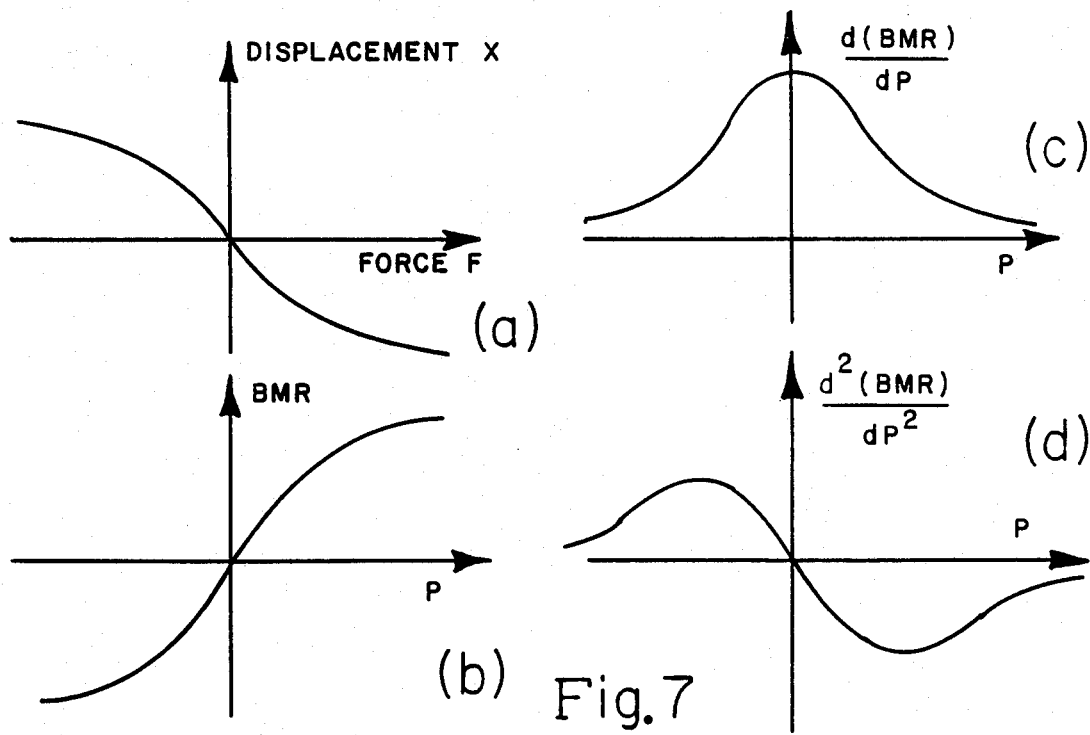
FIGS. 7(a), 7(b), 7(c) and 7(d) show diagrams of Balance Meter Readings (BMR) versus differential pressure P across the implanted sensor and associated derivatives to illustrate how in-vivo calibration of a sensor can be made without using the stop position.

Now it is clear from the above description that the implanted sensor need not have a stop means in it to enable differences in pressures to be determined in-vivo. Thus it could be like the devices shown in FIG. 6 which are dual-diaphragm sensors for epidural ICP monitoring, and single diaphragm devices for intraventricular ICP monitoring. These are identical to the drawings in the referenced patents except they do not have the stop position at zero pressure. All of the numbers in the figure correspond to those in the referenced patents as well. For instance, if at some point the ICP is known and it corresponds to a measured BMR or other apparatus readout parameter, then by the above method a full calibration curve can be determined by applying various positive and negative pressures P(EXT) to the scalp and observing the corresponding BMR or other readout parameter values. Thus, for instance, one could implant a two-diaphragm device such as that in FIG. 2, but without a stop shoulder at a specific pressure, but maintaining the diaphragm coupling by either rigid mechanical coupling means, like a piston or linkage, or the fluid coupling means (a fluid inside the sensor which is incompressible and couples the motion of the two diaphragms by a fluid channel or volume inside the sensor) described in the above patents. Also, in the case of single diaphragm type sensors as illustrated in the above patents and papers, no specific stop position at zero differential pressure need exist for the in-vivo calibration method described here to work. One can even deduce the zero difference pressure point in another way by applying positive and negative pressures on the scalp, as it is this point where one expects to see the curvature of the BMR (or other readout parameter) versus pressure difference P to change from positive to negative. For instance, suppose the BMR is linear or nearly so, versus diaphragm displacement. At the zero point of diaphragm displacement where the diaphragm is relaxed, there is no restoring force within it to tend to drive it toward equilibrium. For displacements to one side or the other, the restricting force F is non-linear, and there is some asymptotic displacement to each side of zero where the force becomes essentially infinite. This is shown in FIG. 7a. This would give a BMR curve versus P (differential pressure on the sensor) like that in FIG. 7b. The first and second derivatives of BMR versus P are shown in FIG. 7c and 7d respectively. Thus, varying P by varying P(EXT) to seek the crossover point in $d^2(BMR)/(dP)^2=0$ would tell you the BMR corresponding to P=0, and thus the full BMR curve versus P would be known. Thus, the use of the method here of varying P(EXT) can be used to calibrate a sensor without the need for a stop position at P=0, even though the stop position makes the in-vivo zero calibration easier in many ways. It is also true that the BMR curve versus P need not be symmetric about zero for the crossover method for curvature to be valid.

This is a specific example of how the in-vivo calibration of a sensor without a stop means could be carried out, but there are other possible specific ways of doing this which are encompassed by the general method of this present invention. Indeed, all of the various device embodiments of my previous referenced patents could be modified to have no stop means at zero pressure and be used in the way described here.

Having described in detail various embodiments of my invention, it will now be apparent to those skilled in the art that numerous modifications can be made therein without departing from the scope of the invention as defined in the following claims.

What I claim and desire to secure by Letter Patent of the United States is:

1. A method for measuring an in-vivo pressure and of calibrating in-vivo a differential pressure sensor, said method comprising:
   (a) implanting in a living body the differential pressure sensor comprising:
     (1) a housing having an opening therein;
     (2) a flexible diaphragm means having a first side and a second side, said flexible diaphragm means extending across said housing opening and being secured with respect to said housing so that, when the sensor is implanted in the living body, the first side of said flexible diaphragm means is in pressure communication with an internal bodily pressure to be measured, and the second side of said flexible diaphragm means is in mechanical pressure communication with the interior side of a portion of skin and thereby in pressure communication across the intact skin with a known variable pressure from a controllable pressure source means external to said living body that is adapted to apply a mechanical pressure to the exterior side of said portion of skin whereby the motion of said flexible diaphragm means is responsive to changes in the difference in said internal bodily pressure and said known external variable pressure;

(3) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means;

(b) remotely detecting the value of the preselected, detectable parameter without any connection to the sensor that requires a break in the skin;

(c) applying a known external variable pressure to said flexible diaphragm means from a controllable pressure source that includes a pressure cuff means adapted to be put in contact with said exterior side of said portion of skin and adapted to supply positive or negative pressures to said portion of skin by placing said pressure cuff in contact with the exterior side of said portion of skin and applying said known external variable pressure to the skin through said pressure cuff with said known external variable pressure being varied over the range of positive and negative values so that simulations of smaller or larger variations of said difference in said internal bodily pressure and said known external variable pressure may be achieved.

2. The method of claim 1 wherein said flexible diaphragm means comprises a multiplicity of pressure responsive diaphragms that are incompressibly motion coupled together, said implanting step comprising implanting said sensor in the living body so that at least one side of one of said pressure responsive diaphragms is in pressure communication with said internal bodily pressure to be measured, and at least one side of one of said pressure responsive diaphragms being in mechanical contact with said interior side of said portion of skin.

3. A method for measuring an in-vivo pressure and of calibrating in-vivo a differential pressure sensor, said method comprising:

(a) implanting in a living body the differential pressure sensor comprising:

(1) a housing having an opening therein;

(2) a flexible diaphragm means having a first side and a second side, said flexible diaphragm means extending across said housing opening and being secured with respect to said housing so that, when the sensor is implanted in the living body, the first side of said flexible diaphragm means is in pressure communication with an internal bodily pressure to be measured, and the second side of said flexible diaphragm means is in mechanical pressure communication with the interior side of a portion of skin and thereby in pressure communication across the intact skin with a known variable pressure from a controllable pressure source means external to said living body that is adapted to apply a positive or negative mechanical pressure to the exterior side of said portion of skin whereby the motion of said flexible diaphragm means is responsive to changes in the difference in said internal bodily pressure and said known external variable pressure;

(3) means for defining a mechanical contact reference position with respect to said housing of said flexible diaphragm means said mechanical contact reference position corresponding to a predetermined relationship between said pressures in communication with said first and second sides of said flexible diaphragm means;

(4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position, and said preselected, detectable parameter changing with a displacement from said mechanical contact reference position of said flexible diaphragm means corresponding to a change in said pressures from said predetermined pressure relationship;

(b) manipulating said sensor by applying a mechanical pressure to the exterior side of said portion of skin to cause said flexible diaphragm means to assume said mechanical contact reference position;

(c) remotely detecting the value of the preselected, detectable parameter when said flexible diaphragm means is at said mechanical contact reference position without any connection to the sensor that requires a break in the skin;

(d) applying a known external variable pressure to said flexible diaphragm means by said controllable pressure source and varying said external variable pressure until the value of said preselected, detectable parameter equals the previously detected value at the mechanical contact reference position at which point said external pressure and said internal bodily pressure has said predetermined pressure relationship, and varying said known external pressure over a range of positive and negative values so as to determine the variation of said preselected, detectable paramter as a function of said external variable pressure and so as to calibrate in-vivo the values of preselected, detectable parameters as a function of the differences in said internal bodily pressure and said known external variable pressure.

4. The method of claim 3 wherein said flexible diaphragm means comprises a multiplicity of pressure responsive diaphragms that are incompressibly motion coupled together, said implanting step comprising implanting said sensor in the living body so that at least one side of one of said pressure responsive diaphragms is in pressure communication with said internal bodily pressure to be measured, and at least one side of one of said pressure responsive diaphragms being in mechanical contact with said interior side of said portion of skin.

5. A method for measuring an in-vivo negative pressure, said method comprising the steps of:
   (a) implanting in a living body a differential pressure sensor comprising:
      (1) a housing having an opening therein;
      (2) a flexible diaphragm means having a first side and a second side, said flexible diaphragm means extending across said housing opening and being secured with respect to said housing so that, when the sensor is implanted in the living body, the first side of said flexible diaphragm means is in pressure communication with an internal bodily pressure to be measured, and the second side of said flexible diaphragm means is in mechanical pressure communication with the interior side of a portion of skin and thereby in pressure communication across the intact skin with a known variable pressure from a controllable pressure source means external to said living body that is adapted to apply a negative mechanical pressure to the exterior side of said portion of skin whereby the motion of said flexible diaphragm means is responsive to changes in the difference in said internal bodily pressure and said known external variable pressure;
      (3) means for defining a mechanical contact reference position with respect to said housing of said flexible diaphragm means, said mechanical contact reference position corresponding to a predetermined relationship between said pressures in communication with said first and second sides of said flexible diaphragm means;
      (4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position, and said preselected, detectable parameter changing with a displacement from said mechanical contact reference position of said flexible diaphragm means corresponding to a change in said pressures from said predetermined pressure relationship;
   (b) varying said known external variable pressure over a range of negative pressure values while detecting said preselected, detectable parameter until said parameter equals said predetermined value at which point said known external variable pressure and said internal bodily pressure have said predetermined pressure relationship.

6. The method of claim 5 wherein said flexible diaphragm means comprises a multiplicity of pressure responsive diaphragms that are incompressibly motion coupled together, said implanting step comprising implanting said sensor in the living body so that at least one side of one of said pressure responsive diaphragms is in pressure communication with said internal bodily pressure to be measured, and at least one side of one of said pressure responsive diaphragms is in mechanical contact with said interior side of said portion of skin.

7. The method of claim 5 wherein said controllable pressure source means includes a pressure cuff means adapted to be put in contact with said exterior side of said portion of skin, said pressure cuff having a flange means on its longer surface which comes into proximity with the skin and which acts to increase the air flow impedance between the region outside the flange and the region inside the flange that is over said exterior side of said portion of skin in order to make more uniform and sustainable said known external negative pressure, and said pressure cuff also adapted with a measuring channel which opens on one end into said region inside the flange and which connects on its other end to a means of measuring said known external negative pressure over said portion of skin, said method further comprising the steps of placing said pressure cuff in contact with the exterior side of said portion of skin and applying said known external negative pressure to the skin through said pressure cuff.

8. The method of claim 7 wherein said controllable pressure source means comprises a partial vacuum source which is connected by a vacuum line to said pressure cuff means, said method further comprising the step of turning on said vacuum source so as to activate and measure said known external negative pressure via said measuring means.

9. The method of claim 8 wherein said vacuum source is a negative pressure or partial vacuum pump means which also has a variable power control to vary the amount of partial vacuum it can supply, said method further comprising the step of varying said variable power control while detecting said preselected, detectable parameter until said parameter approximates said predetermined value.

* * * * *